United States Patent [19]

Trepel et al.

[11] Patent Number: 5,641,500

[45] Date of Patent: Jun. 24, 1997

[54] USE OF PURINERGIC RECEPTOR AGONISTS AS ANTINEOPLASTIC AGENTS

[75] Inventors: Jane B. Trepel; Wei-Gang Fang, both of Bethesda; Farzaneh Pirnia, Potomac; Charles E. Myers, Jr., Rockville, all of Md.

[73] Assignee: The United States of America as represented by the Department of Health and Human Services, Washington, D.C.

[21] Appl. No.: 446,954

[22] Filed: May 15, 1995

Related U.S. Application Data

[63] Continuation of Ser. No. 131,033, Oct. 4, 1993, Pat. No. 5,415,873, which is a continuation of Ser. No. 888,292, May 26, 1992, abandoned, which is a continuation of Ser. No. 509,183, Apr. 16, 1990, abandoned.

[51] Int. Cl.$^6$ .............................. A61K 31/70; A61K 9/08
[52] U.S. Cl. .............................. 424/422; 514/47; 514/48; 514/279
[58] Field of Search .................... 424/422, 573; 514/47, 48, 46, 183, 279

[56] References Cited

U.S. PATENT DOCUMENTS

| | | | |
|---|---|---|---|
| 4,690,935 | 9/1987 | Taylor et al. | 514/356 |
| 4,950,680 | 8/1990 | Taylor et al. | 514/356 |
| 5,415,873 | 5/1995 | Trepel | 424/422 |

OTHER PUBLICATIONS

Rapaport, Eur. J. Cancer. Clinical Oncology, 24, pp. 1491–1497, 1988.

Cusack, Biochem J., 214, pp. 975–981, 1983.

J.R. Fraumeni, Jr. et al, *Principles and Practice of Oncology*, 3rd Edition, 1989.

Kerr, et al, Virchows Arch. Abt. B. Zellpath, "Deletion of Cells by Apoptosis during Castration–Induced Involution of the Rat Prostate", 13:87–102, 1973.

Kyprianou et al, *The Prostate*, "Activation of a $Ca^{2+}$–$Mg^{2+}$–Dependent Endonuclease as an Early Event in Castration–Induced Prostatic Cell Death", 13:103–117 (1988).

Rapaport, *Eur. Cancer Clin. Oncol.*, "Experimental Cancer Therapy in Mice By Adenine Nucleotides", 24:1491–7 (1988).

Smith et al, *Nature*, "Antibodies to CD3/T–cell receptor complex induce death by apoptosis in immature T cells in thymic cultures", vol. 337, pp. 181–184 (1989).

Trepel et al, *Biochem. J.*, "Modulation of bombesin–induced phosphatidylinositol hydrolysis in a small–cell lung–cancer cell line", 225:403–410 (1988).

Ucker, *Nature*, "Cytotoxic T lymphocytes and glucocorticoids activate an endogenous suicide process in target cells", vol. 327, pp. 62–64, 1987.

O'Connor et al, *Trends in Pharmaceutical Sciences*, "Extracellular ATP: effects, sources and fate", 12:137–141, 1991.

Gordon, *Biochem. J.*, 223:309–319, 1986.

Webster's II New Riverside University Dictionary, p. 104, 1984.

Cusack et al, *Biochem. J.*, "Steroselectivity of ectonucleotidases on vascular endothelial cells", 214:975–981, 1983.

(List continued on next page.)

*Primary Examiner*—Gollamudi S. Kishore, PhD
*Attorney, Agent, or Firm*—Morgan & Finnegan, L.L.P.

[57] ABSTRACT

The instant invention is directed to the use of a pharmaceutical composition containing an effective amount of adenosine or an adenosine analog or derivative as an agent useful in the treatment of hormone-independent cancers, such as prostate cancer. The invention is also directed to diagnostic uses of these compounds to determine effective treatment regimes for specific tumors, a process for screening for new, therapeutically useful analogs of these compounds, and the use of these compounds in facilitating the extraction of intracellular components.

16 Claims, 13 Drawing Sheets

OTHER PUBLICATIONS

Mason et al, *Brit. J. Pharmacol.*, "Regulation of transepithelial ion transport and intracellular calcium by extracellular ATP in human normal and cystic fibrosis airway epithelium", 103:1649–1656, 1991.

Moody et al, *Euro. J. Pharmacol.*, "Evidence for the presence of $P_1$-purinoceptors on cholinergic nerve terminals in the guinea-pig illeum", 77:1–9, 1982.

Jay S. Roth, "All About Cancer", published by George F. Stickley Company, p. 14, 1987.

Ogreid et al, *Cancer Research*, "Characterization of the Cyclic Adenosine 3':5'–Monophosphate Effector System in Hormone–dependent and Hormone–independent Rat Mammary Carcinomas", 47: 2576–2582, 1987.

Koschel, *Eur. J. Biochem.*, "A Hormone–independent Rise of Adenosine 3',5'–Monophosphate Desensitized Coupling of β–Adrenergic Receptors to Adenylate Cyclase in Rat Glioma C6–Cells", 108, 163–169, 1980.

Y.J. Bang et al, "Cyclic AMP Induces Transforming Growth Factor Beta-2 Gene Expression and Growth Arrest in the Human Androgen–Independent Prostate Carcinoma Cell Line PC-3"; *Proc. Nat'l Acad. Sci.*, 89(8), pp. 3556–3560, 1992.

W.G. Fang et al, "P-2 Purinergic Receptor Agonsists Inhibit the Growth of Androgen–Independent Prostate Carcinoma Cells", *J. Clin Invest*, 89(1), pp. 191–196, 1992.

Y.J. Bang et al, "Mechanism of Negative Growth Control by Cyclic AMP in a Human Prostate Carcinoma Cell Line Cyclic AMP Induces Production Bioactive TGF–BETA–2 and Underphosphorylation of the Retinoblastoma Protein"; *J. Cell Biochem. Suppl.* 0 (16 Part B), p. 141, Abstract #G305, 1992.

Y.J. Bang et al, "Cyclic AMP Analogs Inhibit the Growth of Human Prostate Carcinoma Cells Evidence For The Role of Transforming Growth Factor–BETA–2; Proc. Am. Assoc. Cancer Res. Annual Meeting," vol. 32, Abstract #326, 1991.

M.A. Oleshansky et al, "Exogenously–Added ATP Promotes Calcium–45 Influx in PC-3M Cells"; *Soc. Neurosci. Abst.* 16(2), p. 1173; Abstract #485.11; 1990.

Y. Sharoni et al, "Effect of Guanine and Adenine Nucleotides on Bombesin–Stimulated Phospholipase C Activity in Membranes From Swiss 3T3 and Small Cell Lung Carcinoma Cells"; *Cancer Res.* 50(17), pp. 5257–5262; 1990.

W.G. Fang et al, "Purinergic Receptor Agonists Stimulate Calcium Mobilization in Human Prostate Carcinoma Cell Lines"; *J. Cell Biochem. Suppl.*, 0 (14 Part B); p. 257; Abstract #F111; 1990.

W.G. Fang et al, "Growth Inhibition of Androgen–Independent Prostate Carcinoma Cells Through Activation of Phospholipase C–Coupled Purinergic Receptors"; Proc. Am. Assoc. Cancer Res. Annual Meeting, 31(0), p. 226; Abstract #1343; 1990.

USE OF PURINERGIC RECEPTOR AGONISTS AS ANTINEOPLASTIC AGENTS

This is a continuation of U.S. Ser. No. 08/131,033 filed Oct. 4, 1993 which issued U.S. Pat. No. 5,415,873 on May 16, 1995, which is a continuation of U.S. Ser. No. 07/888,292 filed May 26, 1992, now abandoned, which is a continuation of U.S. Ser. No. 07/509,183 filed Apr. 16, 1990, now abandoned.

BACKGROUND OF THE INVENTION

1. Field of Invention

The present invention relates to a method for treating hormone-independent cancers via the use of purinergic receptor agonists, diagnostic uses of these compounds to determine effective treatment for specific tumors, a process for screening for new potent analogs of these compounds, and the use of these compounds in facilitating the extraction of intracellular components from cells.

2. Description of Related Art

Prostate cancer is the most common cancer in men and the second most common cause of cancer death in men in the United States (J. F. Fraumeni, Jr. et al. in *Principles and Practice of Oncology*, 3rd edition, 1989, V. T. DeVita, Jr., S. Hellman, and S. A. Rosenberg, eds., J. B. Lippincott, Philadelphia). Approximately 50% of patients are presented with metastatic disease. The only existing treatment for metastatic disease is hormonal therapy, which is not curative. Thus, metastatic disease is uniformly fatal.

Hormonal therapy, which consists of different approaches to blocking the action of androgen on the prostate tumor, is effective in controlling only the growth of tumor cells that depend on androgen for growth (hormone-dependent tumor). Unfortunately, hormone-dependent tumor inevitably progresses to more advanced hormone-independent tumor, which cannot be controlled by current treatment modalities: surgery and radiation therapy are not curative for advanced metastatic disease, and advanced prostatic cancer is not responsive to conventional chemotherapy. New approaches are needed for the treatment of this neoplasm, and any treatment advance would have a significant public health impact.

SUMMARY OF THE INVENTION

The present invention is directed to the use of compounds that act as agonists of the purinergic receptor expressed on androgen-independent cancer cells and inhibit the growth of these cells. It has been discovered that androgen-independent prostate carcinoma cells express purinergic receptors. Furthermore, it has been found that stimulation of these receptors inhibits the growth of these cells. The expression of purinergic receptors on these cells was discovered by inquiry into the nature of the stimulus to which these cells respond after they have escaped androgen control.

This problem was approached by studying signal transductions in androgen-independent human prostate carcinoma cell lines and comparing these responses to those of an androgen-dependent cell line. By incubating the cells in vitro with an agonist of a known cell surface receptor and detecting an intracellular response, it became possible to screen for a wide variety of receptors previously unreported on these cells. $Ca^{2+}$ transients (a rapid, transient increase in the cytoplasmic concentration of unbound calcium) and phosphatidylinositol turnover were employed as the signal transduction system as the prostate is a secretory organ, and $Ca^{2+}$ transients and phosphatidylinositol turnover are critical to the control of other secretory cell types. Cells normally maintain a 10,000 fold lower intracellular $Ca^{2+}$ concentration than extracellular $Ca^{2+}$ concentration, utilizing intracellular energy stores to maintain this differential. Because intracellular $Ca^{2+}$ is maintained at a very low level, hormones that trigger an increase in cytoplasmic free $Ca^{2+}$ are able to affect a large number of intracellular events through the activation of $Ca^{2+}$ dependent enzymes, $Ca^{2+}$ binding proteins, and $Ca^{2+}$ regulated channels. Interestingly, there have not been any reported studies of this signal transduction system in benign or neoplastic prostatic tissue. Thus, the results disclosed here are the first report of (1) hormone-stimulated $Ca^{2+}$ transients in prostatic cells; (2) hormone-stimulated phosphatidylinositol turnover in prostatic cells; (3) purinergic receptor expression on prostatic cells; and (4) purinergic receptor-associated cell death in prostatic adenocarcinoma.

Accordingly, it is an object of the present invention to provide a novel method for effectively treating any hormone independent cancer, including androgen-independent cancers, by employing adenosine or any adenosine derivatives or analogs which are ATP analogs or derivatives. Such cancers include, for example, prostate, ovarian, breast, and endometrial cancer.

Another object of the present invention is to provide diagnostic methods useful for determining treatment modalities for specific tumors.

A further object of the present invention is to provide a method of screening to determine new, functionally potent analogs of purinergic receptor agonists useful in the treatment of hormone-independent cancers.

Yet a further object of the present invention is to provide a method of obtaining intracellular proteins and other components from any cell by exploiting the cell lytic activity of the adenosine derivatives of the present invention.

The foregoing objects and others are accomplished in accordance with the present invention by administering an effective cancer cell growth inhibiting amount of a pharmaceutical composition containing adenosine or an adenosine analog or derivative. Representative adenosine derivatives useful in the present invention include, but are not limited to, adenosine, ATP, ADP, AMP, AMP-PNP, $\alpha,\beta$-methylene ATP, $\beta,\gamma$-methylene ATP, and ATP$\gamma$S, for example.

The therapeutic effect of these compounds can be potentiated by the administration of a $Ca^{2+}$ channel agonist such as the dihydropyridine derivative (-) Bay K 8644. Such $Ca^{2+}$ channel agonists can be administered orally or by continuous or intermittent infusion in an amount effective to achieve a steady-state plasma concentration of from about 0.5 μM to about 500 μM, and a peak plasma concentration from about 500 μM to 2 mM.

The compounds of the present invention can be used for the treatment of human or animal cancers, including cancers of domestic, sport, laboratory, and farm animals. It is contemplated that the inventive compounds will be formulated into a pharmaceutical composition comprising an effective anticancer amount of the compound and a pharmaceutically acceptable carrier. An effective anticancer amount of the pharmaceutical composition will be administered to the subject in a manner which inhibits or prevents tumor growth or metastasis. The amount of the compound and the specific pharmaceutically acceptable carrier will vary depending upon the subject and the condition of this subject, the mode of administration, and the type of cancer being treated, etc.

In a particular aspect, the pharmaceutical composition comprises an effective amount of a purinergic receptor agonist in effective unit dosage form. As used herein, the term "effective unit dosage" or "effective unit dose" is denoted to mean a predetermined anticancer amount sufficient to be effective against the cancer in vivo. Pharmaceutically acceptable carriers are materials useful for the purpose of administering the medicament, which are preferably sterile and non-toxic, and may be solid, liquid, or gaseous materials, which are otherwise inert and medically acceptable, and are compatible with the active ingredients. The pharmaceutical compositions may contain other active ingredients such as preservatives.

These pharmaceutical compositions may take the form of a solution, emulsion, suspension, ointment, cream, granule, powder, drops, spray, tablet, capsule, sachet, lozenge, ampoule, pessary, or suppository. They may be administered by continuous or intermittent infusion, parenterally, intramuscularly, subcutaneously, intravenously, intrathecally, intraarticularly, transdermally, orally, bucally, as a suppository or pessary, topically, as an aerosol, spray, or drops, depending upon whether the preparation is used to treat internal or external cancers. Such administration can be accompanied by pharmacologic studies to determine the optimal dose and schedule to obtain a steady-state plasma concentration from about 0.5 µM to about 500 µM, preferably about 100 µM, a peak plasma concentration from about 500 µM to 2 mM, and to obtain the optimal bone tissue concentration, as would be within the skill of ordinary practitioners. Initial dose escalations from 20 mg/m$^2$ every 8 hours to 500 mg/m$^2$ every 8 hours, with the first dose administered intravenously over one hour, and the subsequent doses administered orally, would be used to determine the maximal therapeutic efficacy and minimum toxicity.

The composition may contain the compound in an amount of from 0.1%–99% by weight of the total composition.

For intravenous injection, the dose may be about 20–500 mg/m$^2$. The solution may contain antioxidants, buffers, etc. If applied topically as a liquid, ointment, or cream, the compound may be present in an amount of about 100 mg to about 500 mg of the composition. For oral administration, the compound should be administered in an amount of about 20 mg/m$^2$ to about 5 g/m$^2$.

The compounds according to the invention may also be formulated for injection and may be presented in unit dose form in ampoules or in multi-dose containers with an added preservative. The composition may take such forms as suspensions, solutions, or emulsions in oily or aqueous vehicles, and may contain formulatory agents such as suspending, stabilizing and/or dispensing agents. Alternatively, the active ingredient may be in powder form for consitution with a suitable vehicle, e.g., sterile, pyrogen-free water, before use.

Alternatively, for cancers of the skin, or other external tissues, the compositions are preferably applied to the affected part of the body of the patient as a topical ointment or cream. The compounds may be presented in an ointment, for instance with a water soluble ointment base, or in a cream, for instance with an oil in water cream base, in a concentration of from about 100 mg/L to 500 mg/L.

The compounds may also be applied into body orifices such as the nose, oral cavity, and ears in the form of spray or drops. They may be applied into body orifices such as the rectum and vagina in the form of a suppository or cream.

It will be appreciated that extensive skin cancers may require the use of higher doses.

For systemic administration, the daily dosage as employed for adult human treatment will range from 20 mg/m$^2$ to 2 g/m$^2$, which may be administered in 1 to 5 daily doses, for example, depending on the route of the administration and the condition of the patient.

Since a Ca$^{2+}$ transient in response to P$_2$ purinergic agonists is characteristic of advanced, androgen-independent prostate cancer, this analytical method can be used to screen for advanced cancers that are amenable to treatment with purinergic receptor agonists. For example, specimen cells of such cancers can be tested for expression of P$_2$ purinergic receptors by use of labeled ligand, anti-receptor antibody, or by a molecular probe. In addition, cells from fresh specimens can be assayed for Ca$^{2+}$ mobilization in response to P$_2$ agonists.

The methods of the present invention also provide a means for screening of new, potent, analogs or derivatives of purinergic receptor agonists therapeutically useful in treating hormone-independent cancers. This can be accomplished, for example, by testing for rapid, transient increases in cytoplasmic free Ca$^{2+}$ in human androgen-independent prostate carcinoma cells. This technique can be applied to any individual patient biopsy, providing an in vitro assay for optimal individual treatment design, and includes flow cytometric analysis of single cells.

Finally, the method of the present invention can be used to recover intracellular components. The induction of slow, programmed cell death and lysis by P$_2$ agonists can facilitate the harvesting and recovery of cell organelles, proteins, etc.

BRIEF DESCRIPTION OF THE DRAWINGS

The invention is further illustrated in the accompanying drawings, wherein:

FIG. 5A=ATP; FIG. 5B=AMP-PNP (5'adenylylimidodiphosphate); FIG. 5C=$\alpha,\beta$-methylene ATP (Adenylyl [$\alpha,\beta$-methylene]-diphosphonate), R=P(O)(OH) O$^-$, B=Adenine; FIG. 5D=$\beta$, $\gamma$-methylene ATP (Adenylyl [$\beta,\gamma$-methylene]-diphosphonate); FIG. 5E=ATPγS (Adenosine-5'O-[3-thiophosphate]).

DETAILED DESCRIPTION OF THE INVENTION

CELLS

Figure 1:
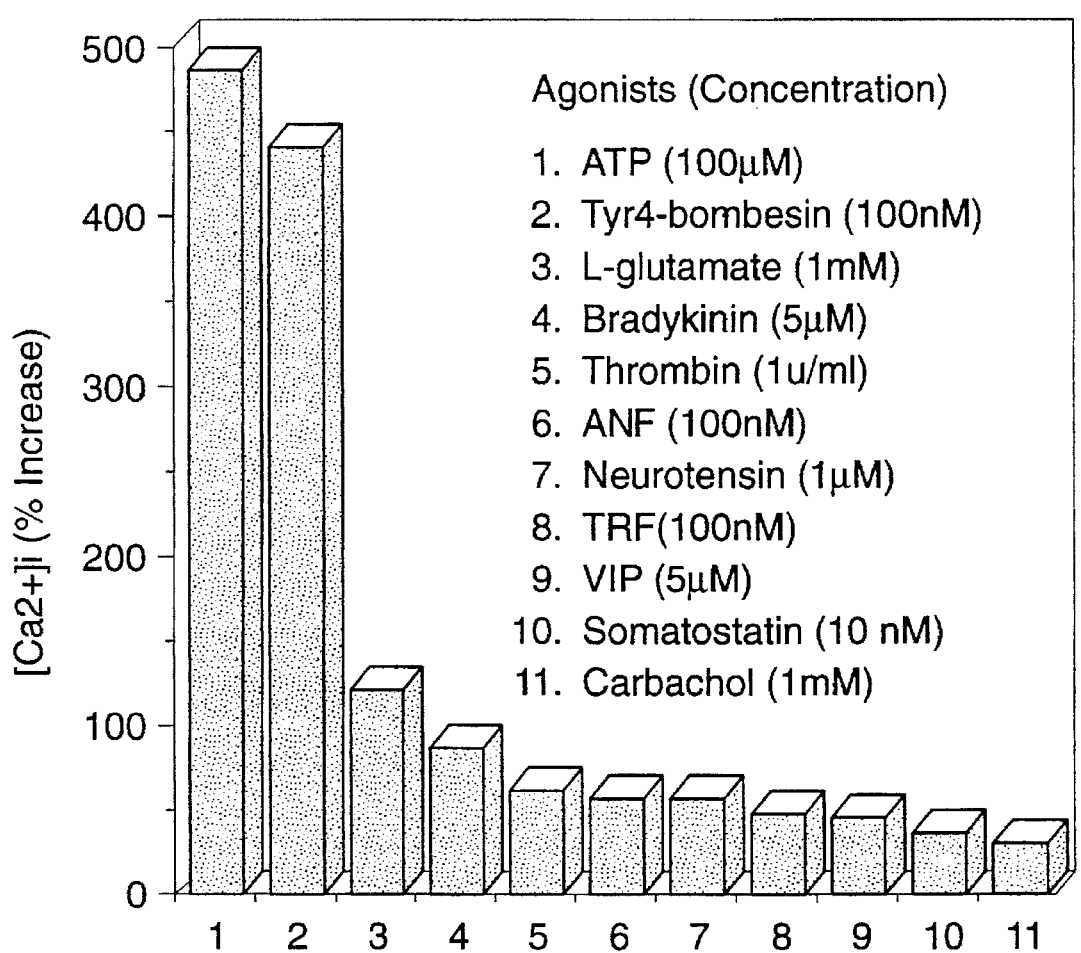
FIG. 1 shows the Ca$^{2+}$ mobilizing activity of various peptides and neurotransmitters in PC-3 prostate carcinoma cells.

The human prostate carcinoma cell lines PC3, DU145 (American Type Culture Collection) and PC-3M (a gift of Dr. G. Weiss, Surgery Branch, NCI) were maintained in Ham's F12K (PC3), Eagle's Modified Essential Medium (DU145), or RPMI 1640 (PC3M), supplemented with 7% (PC3) or 10% (DU145 and PC3M) fetal bovine serum, 100 units/ml penicillin, 100 mg/ml streptomycin, and 300 mg/ml glutamine. The cells were grown in a mixture of 5% $CO_2$, 95% air at 37° C., and propagated by typsinization and dilution into fresh medium. Cells were typically used for calcium determination two days after dilution into fresh medium.

MEASUREMENT OF INTRACELLULAR FREE CALCIUM $[Ca^{2+}]_i$;

$[Ca^{2+}]_i$ was determined by the quin2 technique of Tsien et al. (J. Cell Biol. 94:325–334, 1982) with some modifications. Briefly, cells from confluent cultures were harvested by treatment with trypsin-EDTA. Cells were washed with calcium medium (1 mM $CaCl_2$, 1 mM KCl, 1 mM $MgCl_2$, 140 mM NaCl, 20 mM HEPES, 5 mM dextrose, pH 7.4), and loaded with 20 mM quin2/AM (Molecular Probes, Eugene, Oreg.) in calcium medium at 37° C. for 30 minutes, then diluted 5-fold with the same medium and incubated at 37° C. for 60 minutes. After loading, cells were washed and resuspended in the calcium media at $1.5–2.0 \times 10^6$ cells/ml and kept on ice until use. Cell viability was determined by trypan blue exclusion and was usually >95%. For measurement of fluorescence, 2 ml of cell suspension was transferred to a cuvette maintained at 37° C. Fluorescence was measured in a Perkin-Elmer 650-10S fluorescence spectrophotometer, with an excitation wavelength of 336 nm, slit 5 nm, and an emission wavelength of 493 nm, slit 5 nm. $[Ca^{2+}]_i$ was estimated after calibration with Triton X-100 and EGTA, assuming a dissociation constant of the $Ca^{2+}$-quin2 complex of 115 nM.

Flow cytometric studies were performed allowing analysis of the $Ca^{2+}$ response at the single cell level. These studies demonstrated purinergic receptor stimulated $Ca^{2+}$ transients in prostate carcinoma cells, and showed marked heterogeneity within the PC-3 cell line in the purinergic response.

FLOW CYTOMETRIC ANALYSIS OF THE $Ca^{2+}$ RESPONSE IN SINGLE CELLS

Cells were prepared as described above. The loading procedure was performed by incubating cells with 1 uM Fluo-3 (Molecular Probes, Eugene, Oreg.), a recently described long wavelength calcium indicator (Tsien et al., J. Biol. Chem. 264:8171,1989). Cells were incubated at room temperature for 30–60 min., washed, and resuspended in calcium medium. Rabbit anti-fluorescein antibody (1 unit/ml, Molecular Probes) was added to the cell suspension to reduce fluorescence background. Fluorescence was measured using a Becton-Dickinson FACStar equipped with a 5 watt argon laser, using 488 nm excitation. Parallel studies were performed by fluorescence spectrophotometry (excitation 506 nm, slit 5 nm, emission 526 nm, slit 5 nm).

The biochemical pathway activated by purinergic receptor stimulation in prostate carcinoma cells was studied further by assay of phospholipase C activity. These studies demonstrated that purinergic receptor stimulation induces phospholipase C activity and breakdown of phosphatidylinositol bisphosphate to inositol trisphosphate, which interacts with a specific inositol trisphosphate receptor and releases $Ca^{2+}$ from internal stores.

METABOLISM OF [$^3$H]INOSITOL PHOSPHATES

Cells were incubated with $^3$H-inositol (6 µCi/ml) in inositol-free RPMI 1640 medium (NIH Media Unit) without serum for 2 to 3 days at 37° C. under an atmosphere of 5% $CO_2$, 95% air. Cells were detached by trypsinization, washed twice in phosphate buffered saline pH 7.4, resuspended in PBS with 10 mM LiCl, and maintained for 15 minutes at 37° C. After that, cells were washed twice with PBS plus 10 mM LiCl and resuspended in calcium medium plus 10 mM LiCl. The cell suspension was aliquoted into Eppendorf tubes, pre-warmed at 37° C., and treated with reagents for different times as indicated. Reactions were terminated by adding 100% trichloroacetic acid (TCA) to a final concentration of 10%. After centrifugation, the supernatants were removed, extracted twice with water-saturated ether to remove TCA, and stored at 4° C. until quantitative analysis of inositol phosphates by high pressure liquid chromatography.

ANALYSIS OF INOSITOL PHOSPHATES BY HIGH PRESSURE LIQUID CHROMATOGRAPHY

Samples prepared as described above were applied to a Whatman Partisil 5 SAX column. Inositol phosphates were separated using an ammonium phosphate gradient (0.01M to 1.4M. pH 3.8, 1 ml/min flow rate) as described previously (Biochem. J. 255: 403–410, 1988). Radioactivity was measured by use of a Raytest radiodetector with a 2 ml flow cell and a ratio of 4:1 (v:v) of Monoflow 4 high salt scintillant (National Diagnostics); eluate at an efficiency of 17%. Values (counts/min) for each inositol phosphate were expressed as a percentage of $^3$H-phosphoinositides in the sample, permitting comparison among experiments.

STUDIES OF CELL GROWTH INHIBITION AND APOPTOSIS

Cell growth was studied by hemacytometer counts of viable cells after incubation of cells with purinergic agonists in vitro. Viability was determined by trypan blue exclusion. In addition, growth studies were performed by $^3$H-thymidine incorporation. These studies showed that over a period of 5 days, purinergic agonists stimulated $^3$H-thymidine incorporation on a per cell basis while inhibiting cell growth. These data suggested that purinergic agonists are stimulating DNA strand breaks and DNA repair. The induction of DNA strand breaks in the setting of cell growth inhibition is characteristic of programmed cell death or apoptosis.

NUDE MOUSE STUDIES

PC-3 prostate carcinoma cells were treated in vitro with the puringeric agonists ATP or AMP-PNP, 100 uM 3 times over 7 days, and their growth in athymic mice was compared to that in untreated control cells. Cells were injected subcutaneously at an inoculum of $1.5 \times 10^6$ cells/mouse in 0.2 ml phosphate buffered saline, and the presence of palpable tumors was determined on day 22.

RESULTS

EFFECT OF ATP ON PROSTATE CARCINOMA CELL LINES

Figure 2:
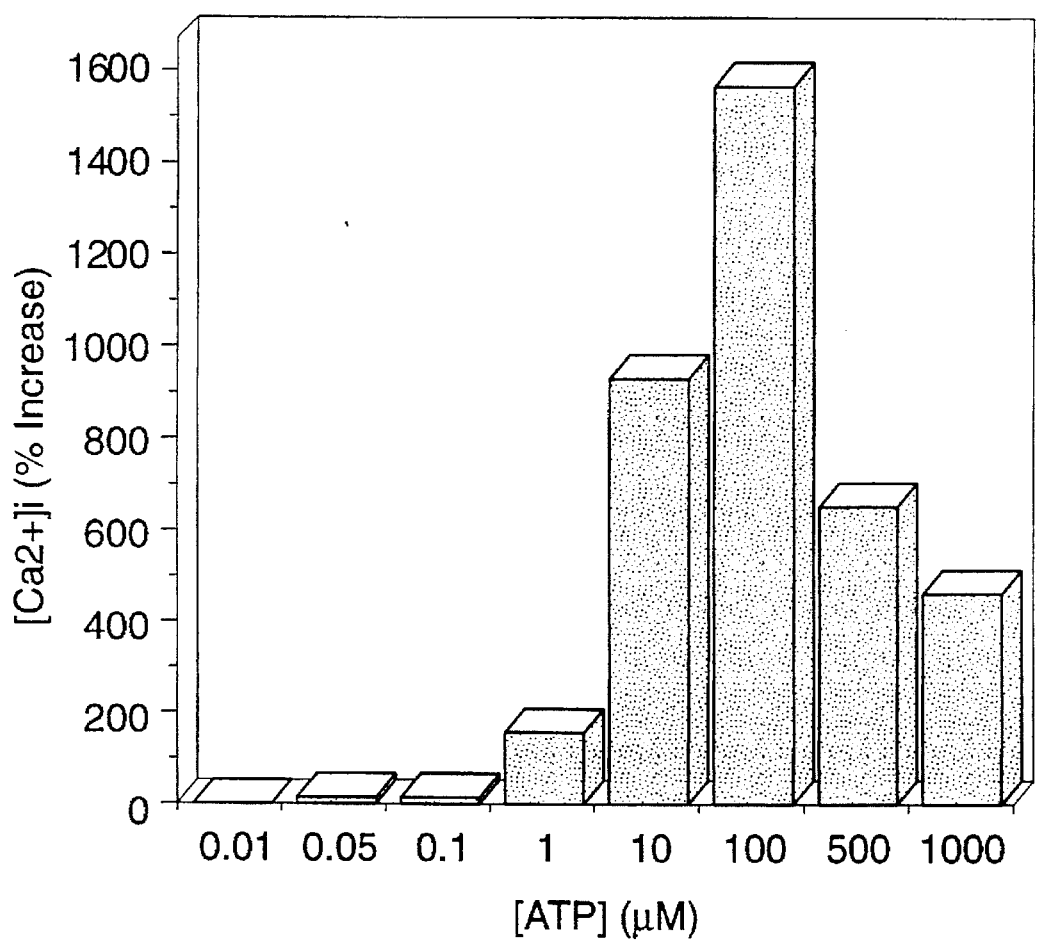
FIG. 2 shows the concentration dependence of the ATP-stimulated Ca$^{2+}$ response for the androgen-independent prostate carcinoma cell line DU145. In 13 experiments using DU145 treated with 100 µM ATP, the mean percent stimulation was 510.7, with a range from 77.7 to 1690.8%.
Figure 3:
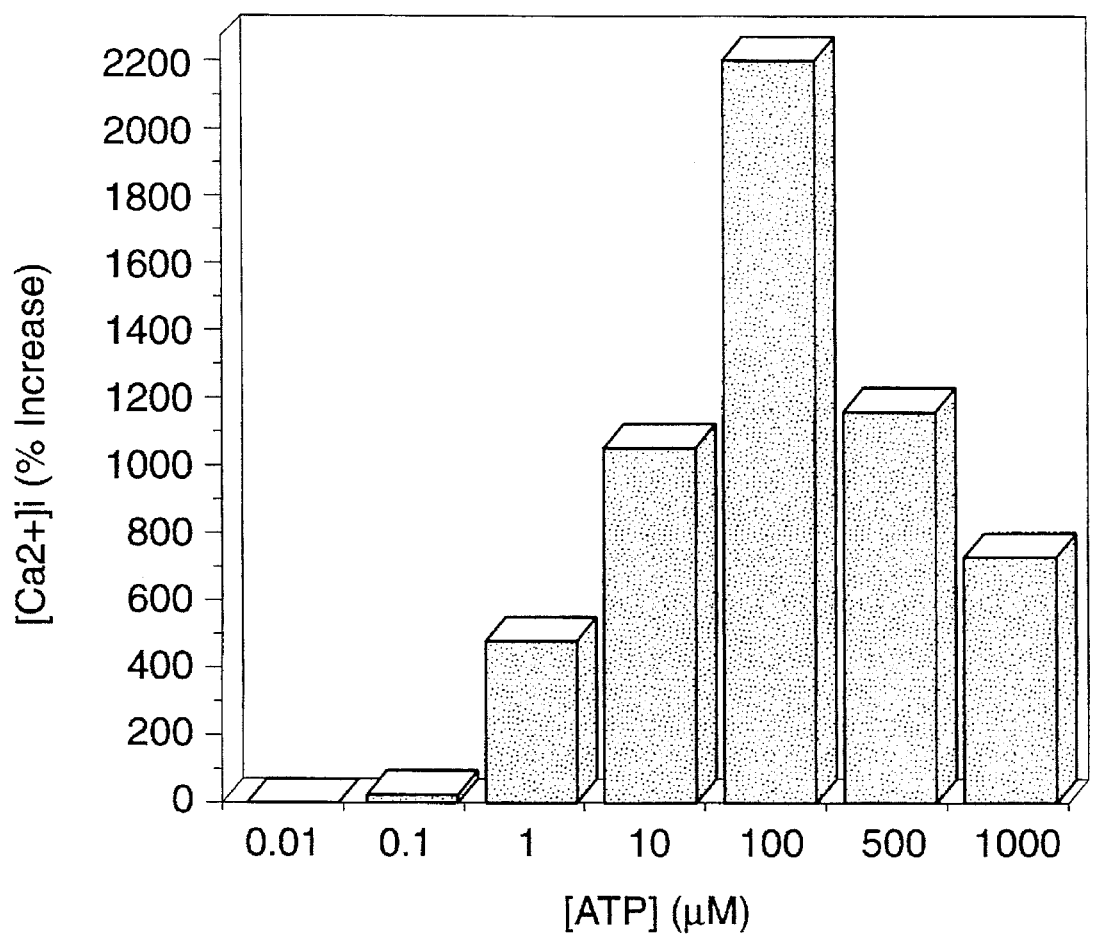
FIG. 3 shows the concentration dependence of the ATP-stimulated Ca$^{2+}$ response for the androgen-independent prostate carcinoma cell line PC-3. In 16 experiments using PC-3 treated with 100 µM ATP, the mean percent stimulation as 443.3, with a range from 101.5 to 2284%.
Figure 4:
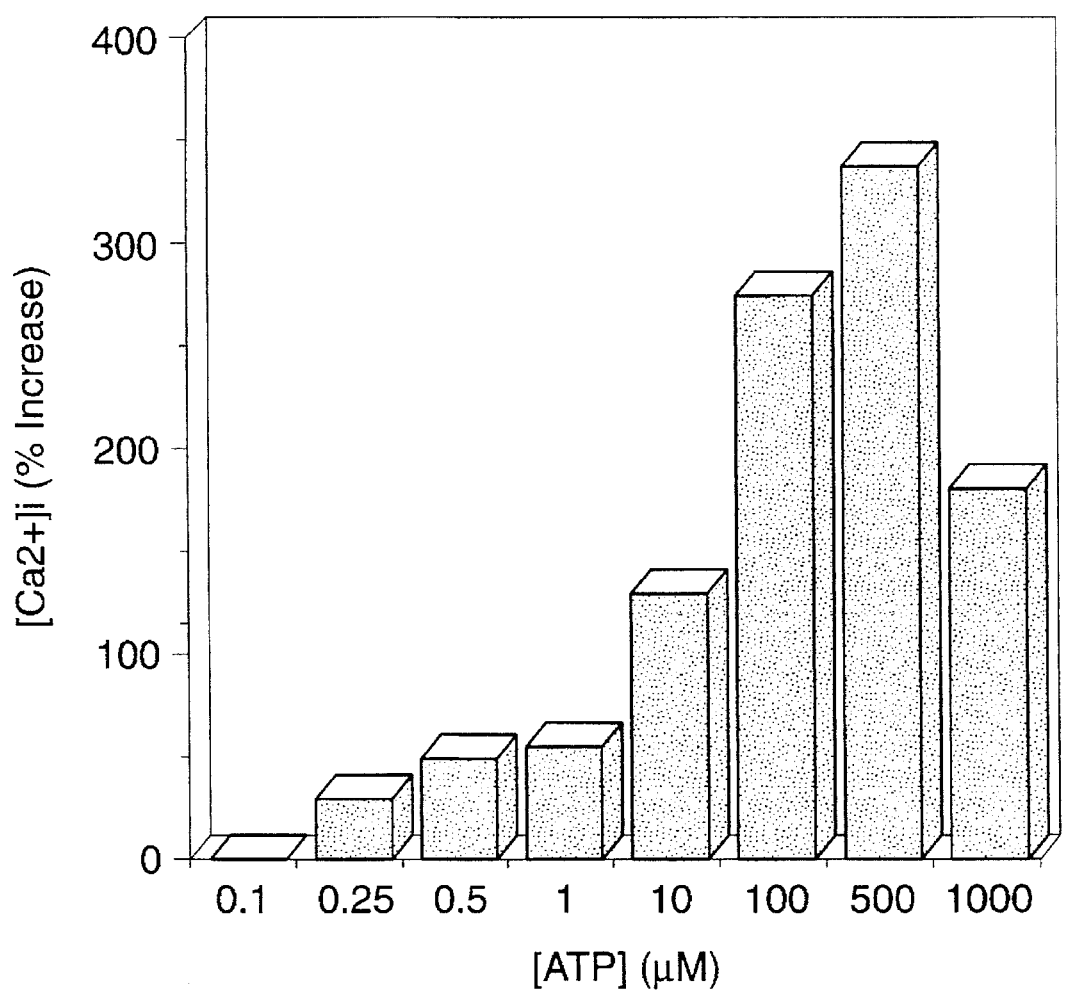
FIG. 4 shows the concentration dependence of the ATP-stimulated Ca$^{2+}$ response for the androgen-independent prostate carcinoma cell line PC-3M.
Figure 5A:
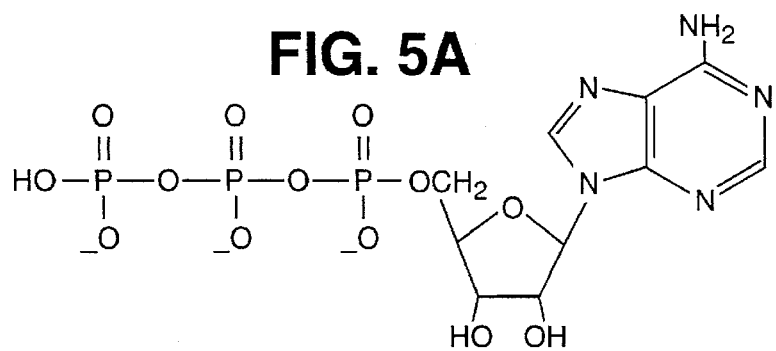
FIG. 5A through FIG. 5E shows a series of adenine nucleotides with modified phosphate groups.
Figure 5B:
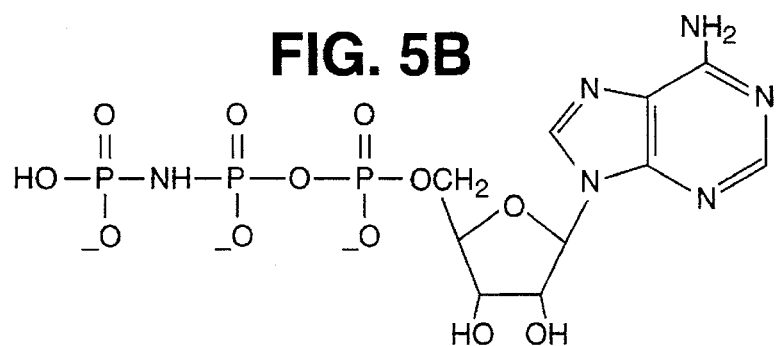
Figure 5C:
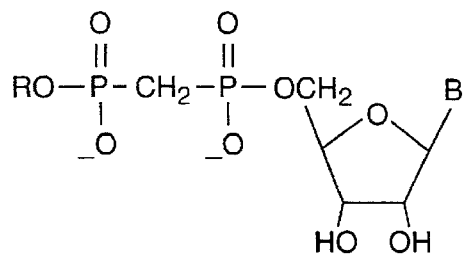
Figure 5D:
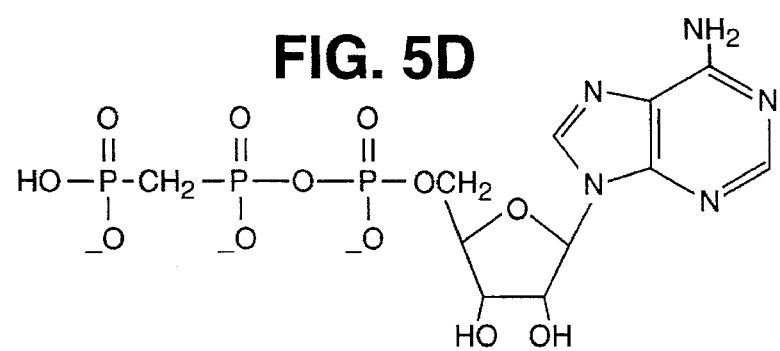
Figure 5E:
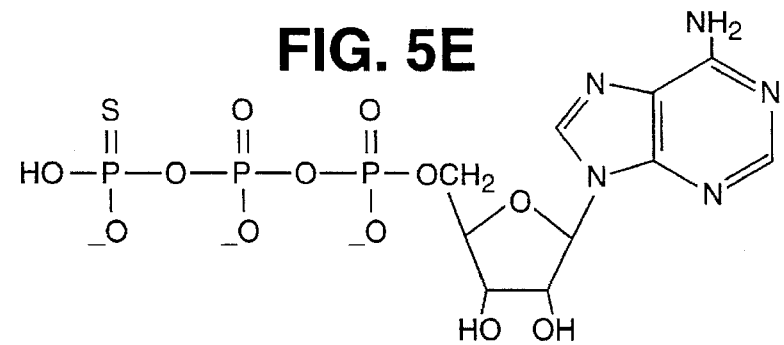

A wide variety of surface receptors that induce an increase in $[Ca^{2+}]_i$ was found (FIG. 1). These are novel observations for two reasons. Firstly, the presence of these receptors on prostate carcinoma cells has not been reported. Secondly, these are the first studies showing hormone-activated $Ca^{2+}$ transients in prostatic tissue. The first studies of the biological effects of the $Ca^{2+}$ response were directed to an examination of the effect of ATP on the prostate carcinoma cell lines. Aside from its role in cell metabolism, ATP is now known to act extracellularly at specific plasma membrane receptors called purinergic receptors or purinoceptors. As can be seen from FIG. 1, ATP produces the largest $Ca^{2+}$ response of the agonists tested. This response is so large in the prostate carcinoma cells that there is almost complete depletion of internal $Ca^{2+}$ stores. The concentration-dependence of the ATP-stimulated $Ca^{2+}$ response is shown for the androgen-independent prostate carcinoma cell lines DU145 (FIG. 2), PC-3 (FIG. 3), and PC-3M (FIG. 4). These three cell lines are the only well characterized human androgen-independent prostate carcinoma cell lines, and all three showed a strong purinergic response. There is one hormone-sensitive prostate carcinoma cell line, LNCaP, which was tested and found to lack a purinergic response (data not shown). Purinergic receptors are expressed on a wide variety of cell types, ranging from hematopoietic cells to endothelial cells. These data are the first description of purinergic receptors on benign or neoplastic prostate cells, however, and suggest that the purinergic receptors identified may be specifically expressed on advanced, hormone-refractory prostatic carcinoma cells.

PHOSPHOLIPASE C STUDIES

Hormone-stimulated $Ca^{2+}$ transients are thought to be induced by activation of phospholipase C, an enzyme that catalyzes the hydrolysis of phosphatidylinositol bisphosphate to diacylglycerol and inositol trisphosphate, and inositol trisphosphate-mediated release of $Ca^{2+}$ from internal $Ca^+$ storage vesicles. Whether ATP acts through stimulation of phospholipase C has been determined by high pressure liquid chromatographic analysis of inositol phosphate metabolites in metabolically labeled prostate carcinoma cells (see above, Metabolism of [$^3$H] Inositol Phosphates by PC-3 and DU145 Cells). The data in Table 1 show a representative experiment performed in PC-3 cells, demonstrating ATP-stimulated phospholipase C activity. These data are the first to show hormone-stimulated phosphatidylinositol turnover in prostatic cells, and identify the signal transduction pathway activated by purinergic agonists in prostatic carcinoma cells.

TABLE 1

ATP-STIMULATED INOSITOL PHOSPHATE PRODUCTION IN PC-3 PROSTATE CARCINOMA

| | I(1,4,5)P3 cpm | % of total IP |
|---|---|---|
| 8 sec Control | 569 | 0.33 |
| ATP | 1103 | 0.64 |
| 15 sec Control | 318 | 0.19 |
| ATP | 971 | 0.57 |
| 30 sec Control | 794 | 0.46 |
| ATP | 1361 | 0.78 |

TESTING OF VARIOUS PURINE ANALOGS

Figure 6:
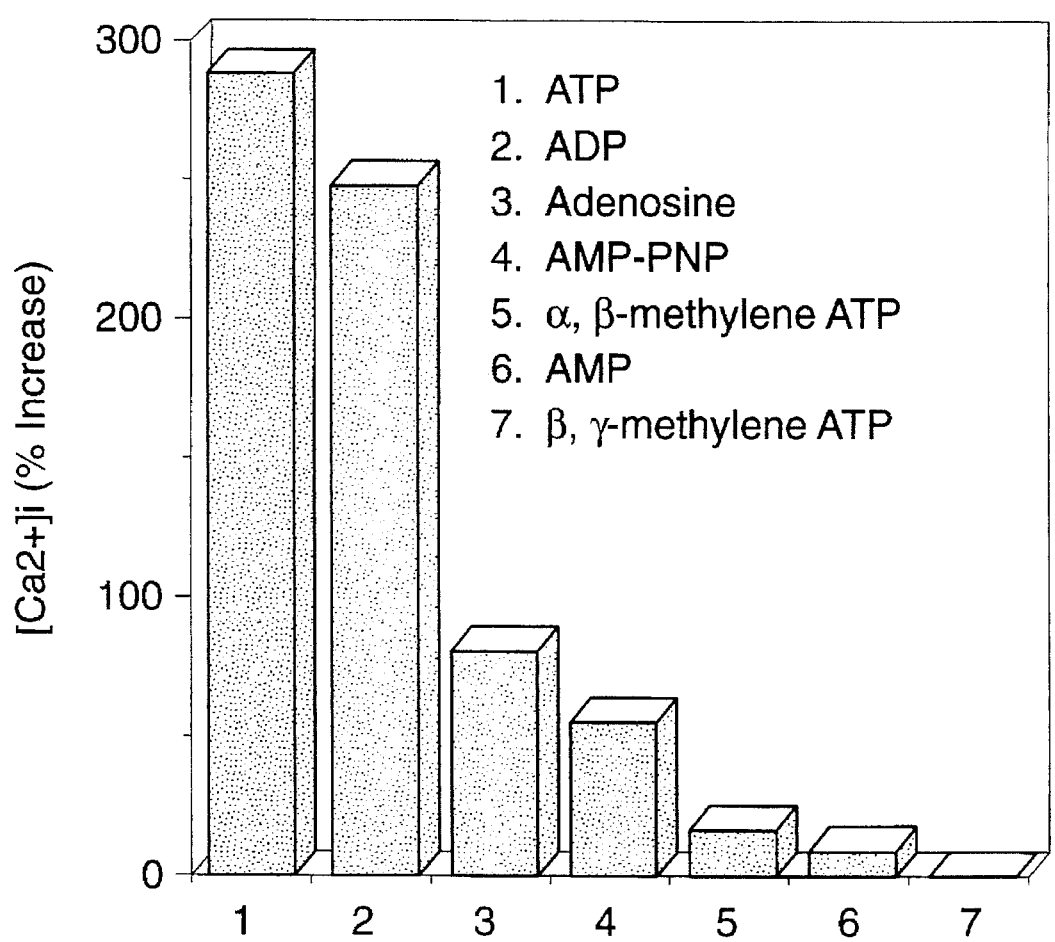
FIG. 6 shows the pharmacologic characterization of the DU145 prostate carcinoma purinergic receptor.
Figure 7:
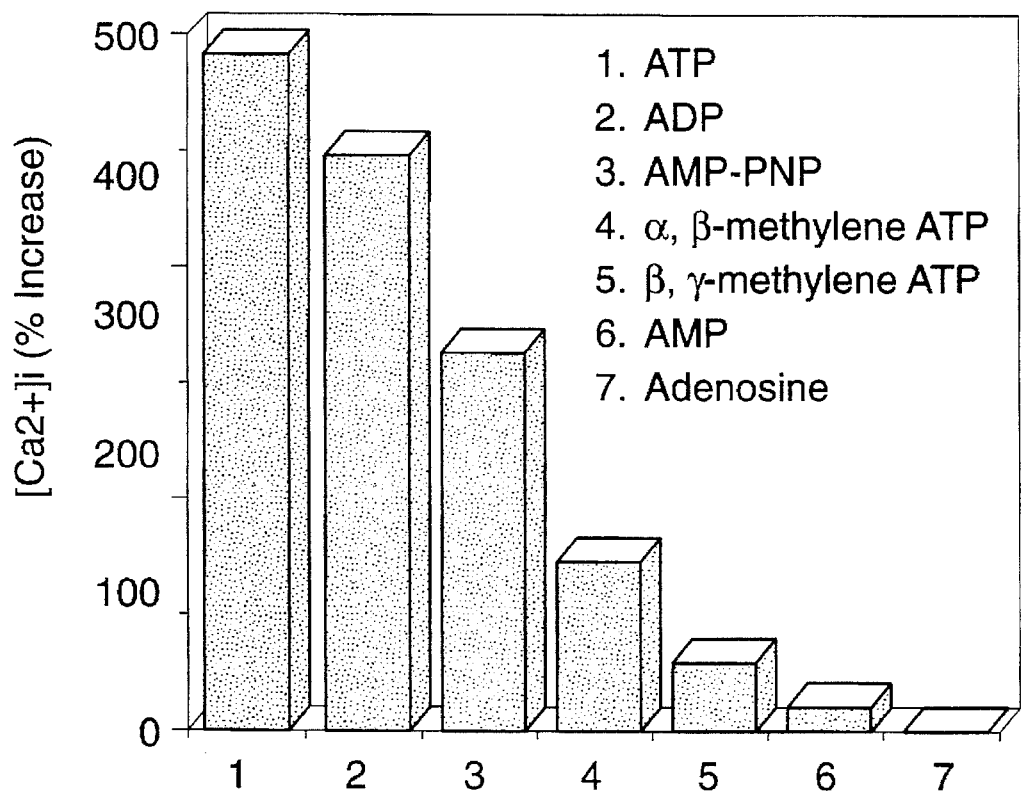
FIG. 7 shows the pharmacologic characterization of the PC-3 prostate carcinoma purinergic receptor.
Figure 8:
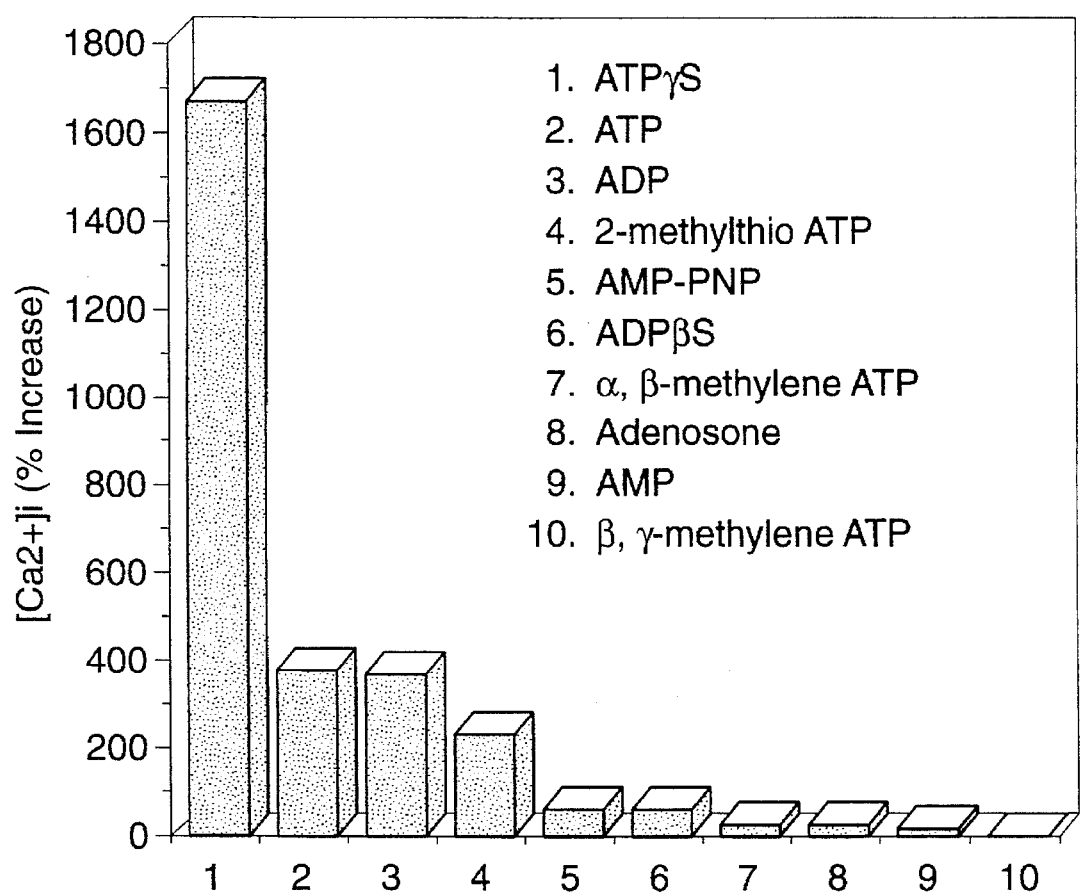
FIG. 8 shows the pharmacologic characterization of the purinergic receptor on PC-3M prostate carcinoma cells.

Purinergic receptors have been divided into different subtypes pharmacologically, on the basis of the order of potency of different purine compounds. In order to characterize the purinergic receptor on the prostate carcinoma cells, a series of purines was tested for their relative potency in inducing a $Ca^{2+}$ transient. These compounds included the well known, commercially available purines ATP (adenosine triphosphate), ADP (adenosine diphosphate), AMP (adenosine monophosphate), and adenosine, as well as the lesser known, commercially available compounds shown in FIG. 5A through FIG. 5E. The compounds shown in FIG. 5B through FIG. 5E are adenine nucleotides with modified phosphate groups. Each of these modifications should increase the resistance of the compound to hydrolysis, and thus increase the usefulness of the compound as a therapeutic agent. The results of studies measuring the $Ca^{2+}$ response to these compounds are shown in FIG. 6 (DU145), FIG. 7(PC-3), and FIG. 8 (PC-3M). The data for each of these cell lines show expression of a $P_2$ subtype purinergic receptor, for which the more highly phosphorylated purines are most active, following the general scheme of agonist potency ATP>ADP>AMP>adenosine, as opposed to $P_1$ purinergic receptors, for which adenosine>AMP>ADP>ATP. These figures also disclose that the non-hydrolysable analogs have agonist activity. Thus, the non-hydrolysable compounds should recognize androgen-independent prostate cancer in vivo, and therefore be therapeutically useful.

STUDIES WITH $Ca^{2+}$ CHANNEL BLOCKERS

Figure 9:
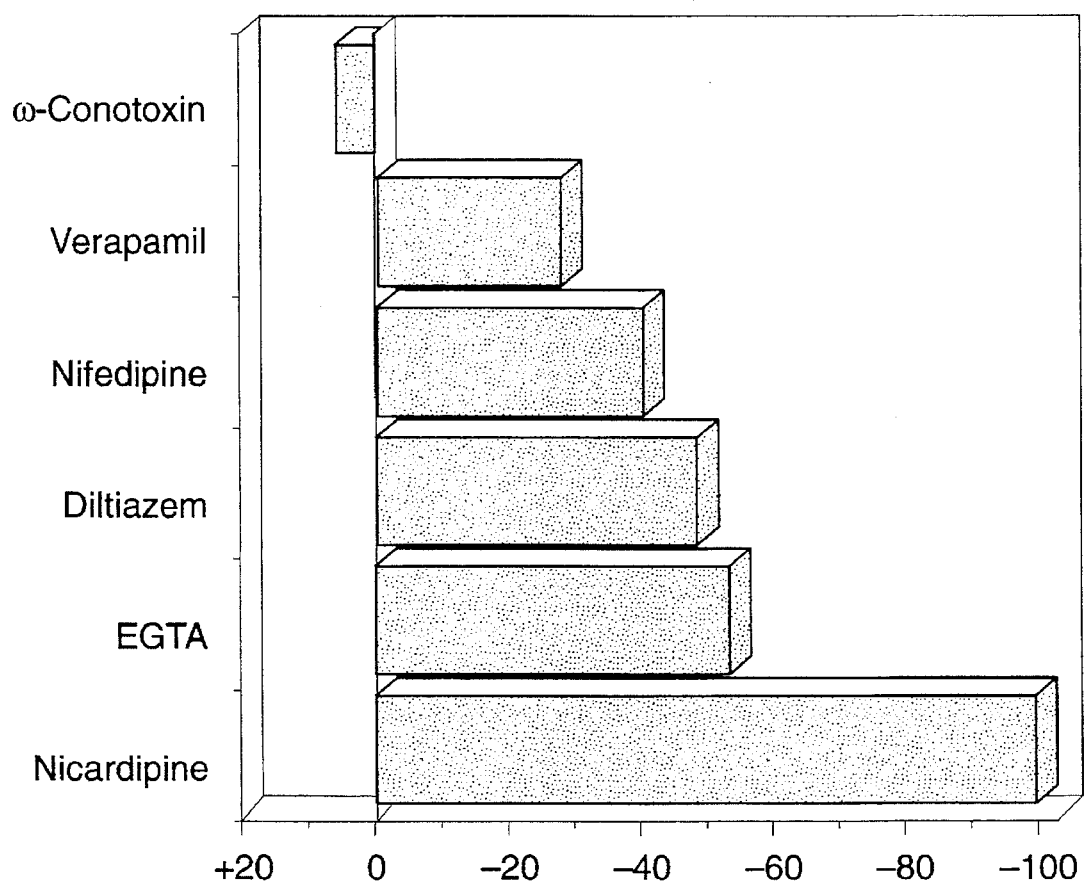
FIG. 9 shows the effect of organic Ca$^{2+}$ channel blockers on the ATP-stimulated Ca$^{2+}$ transient in PC-3 prostate carcinoma cells.

It was found that the increase in cytoplasmic free $Ca^{2+}$ induced by purinergic agonists is derived both from release of $Ca^{2+}$ from internal stores and from the opening of plasma membrane $Ca^{2+}$ channels on the prostate carcinoma cells. The opening of these channels serves to prolong the $Ca^{2+}$ response to purinergic agonists by allowing influx of $Ca^{2+}$ from the external milieu into the cell. These channels were characterized pharmacologically because a compound that opens such channels could be used in combination with the purinergic agonist to increase the therapeutic response. The channel was characterized by using specific, commercially available $Ca^{2+}$ channel blockers to inhibit the influx of extracellular $Ca^{2+}$ caused by ATP stimulation of the prostate carcinoma cell lines. The data in FIG. 9 show that the channel is inhibitable by the dihydropyridine class of $Ca^{2+}$ channel blocker (nicardipine and nifedipine), by the phenylalkylamine class of channel blocker (verapamil), and by a benzothiazepine (diltiazem), but not by the peptide $Ca^{2+}$ channel blocker ω-conotoxin. These data are the first characterization of the $Ca^{2+}$ channel expressed on the surface of prostate carcinoma cells.

SIGNAL TRANSDUCTION STUDIES IN INDIVIDUAL CELLS

Figure 10A:
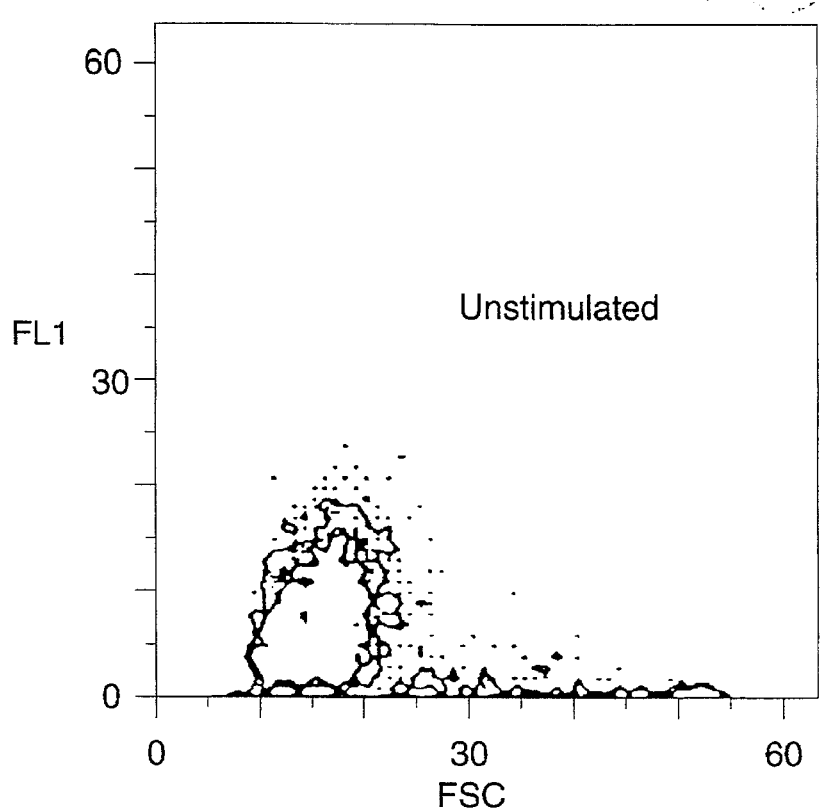
FIG. 10A and FIG. 10B shows contour plots obtained by flow microfluorometric analysis of unstimulated (FIG. 10A) and ATP-stimulated (FIG. 10B), $Ca^{2+}$ mobilization in PC-3 prostate carcinoma cells. These contour plots demonstrate the heterogeneity of the ATP response in the PC-3 cell line. X-axis: forward angle light scatter (measure of cell size) Y-axis: fluorescence intensity, linear scale (measure of $[Ca^{2+}]_i$). Z-axis: cell number.
Figure 10B:
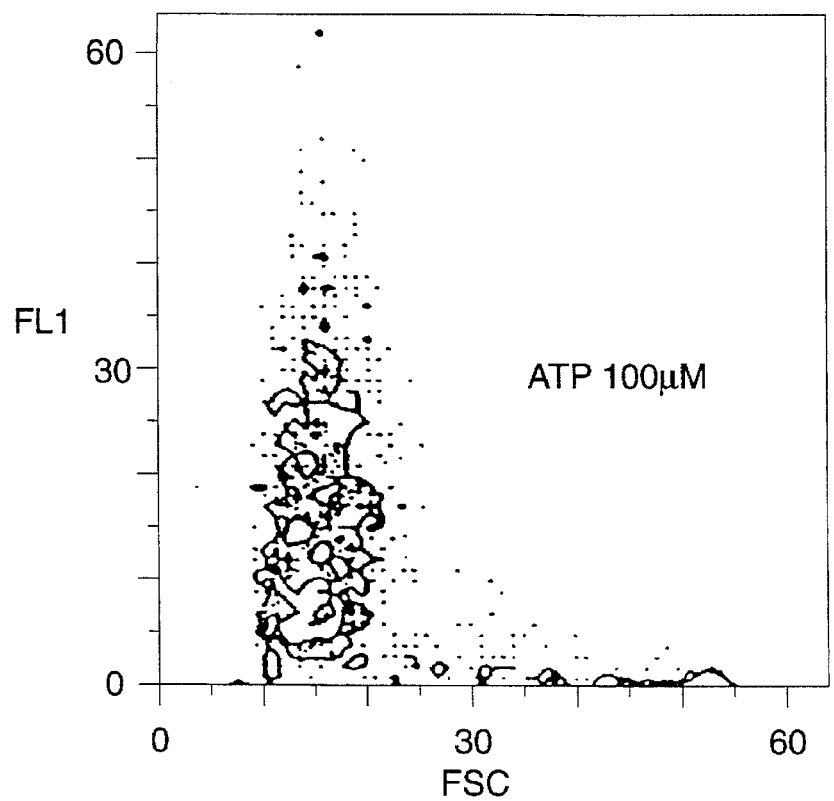

The signal transduction studies that have been performed are studies of the response of many cells in a suspension. The purinergic response of individual cells has also been assessed to determine the purinergic response of individual cells to determine the degree of intratumor heterogeneity. These experiments were performed by flow cytometric analysis of the $Ca^{2+}$ response, using a laser-activated flow microfluorometer (see above, Flow Cytometric Analysis of the $Ca^{2+}$ Response in Single Cells). The contour plots in FIG. 10B show that there is heterogeneity in the purinergic responsiveness of the PC-3 prostate carcinoma cell line. This technique is a useful adjunct for screening for therapeutically effective compounds because it allows the analysis of signal transductions on a single cell basis.

EFFECT OF PURINERGIC RECEPTOR STIMULATION ON THE GROWTH OF ANDROGEN-INDEPENDENT CELLS.

Figure 11:
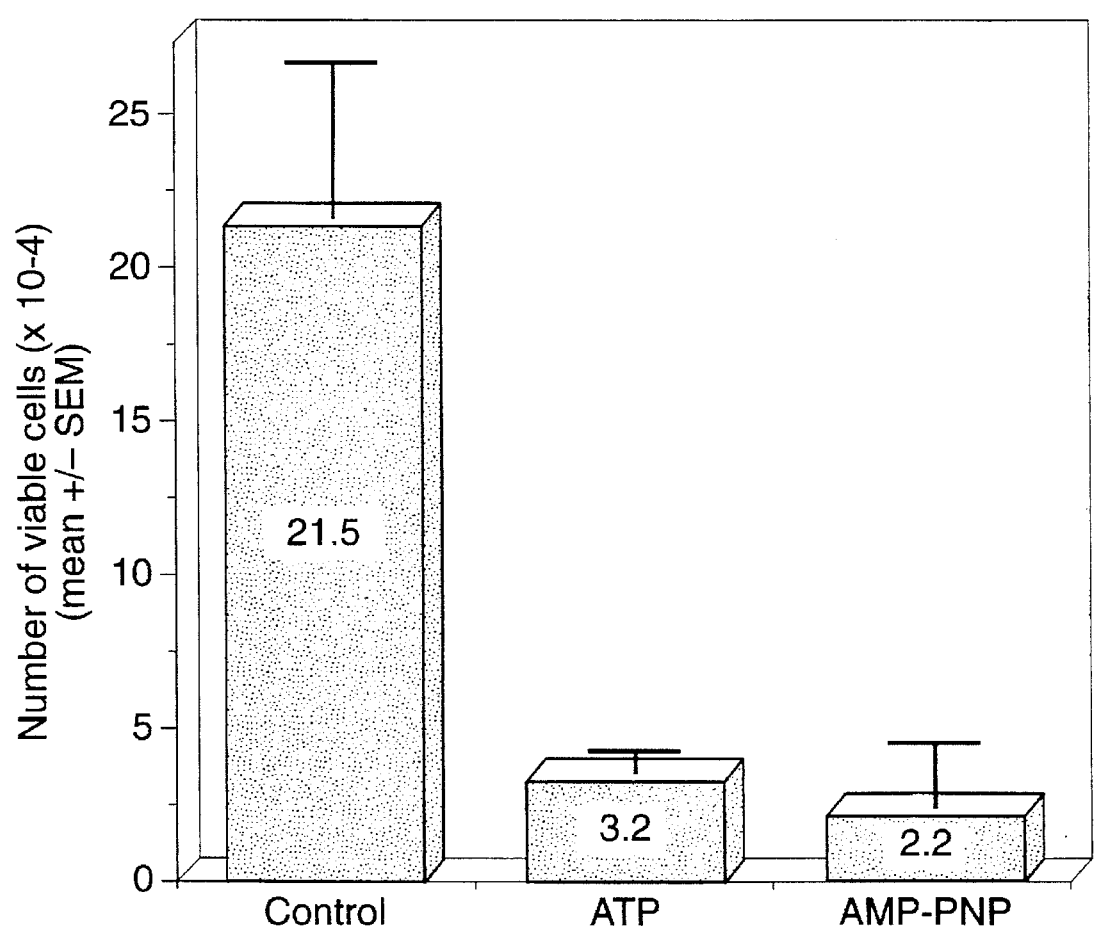
FIG. 11 shows the inhibition of growth of DU145 cells in the presence of ATP and AMP-PNP. Cultures incubated for 5 days in the presence of 100 µM ATP or 100 µM AMP-PNP versus untreated controls.
Figure 12:
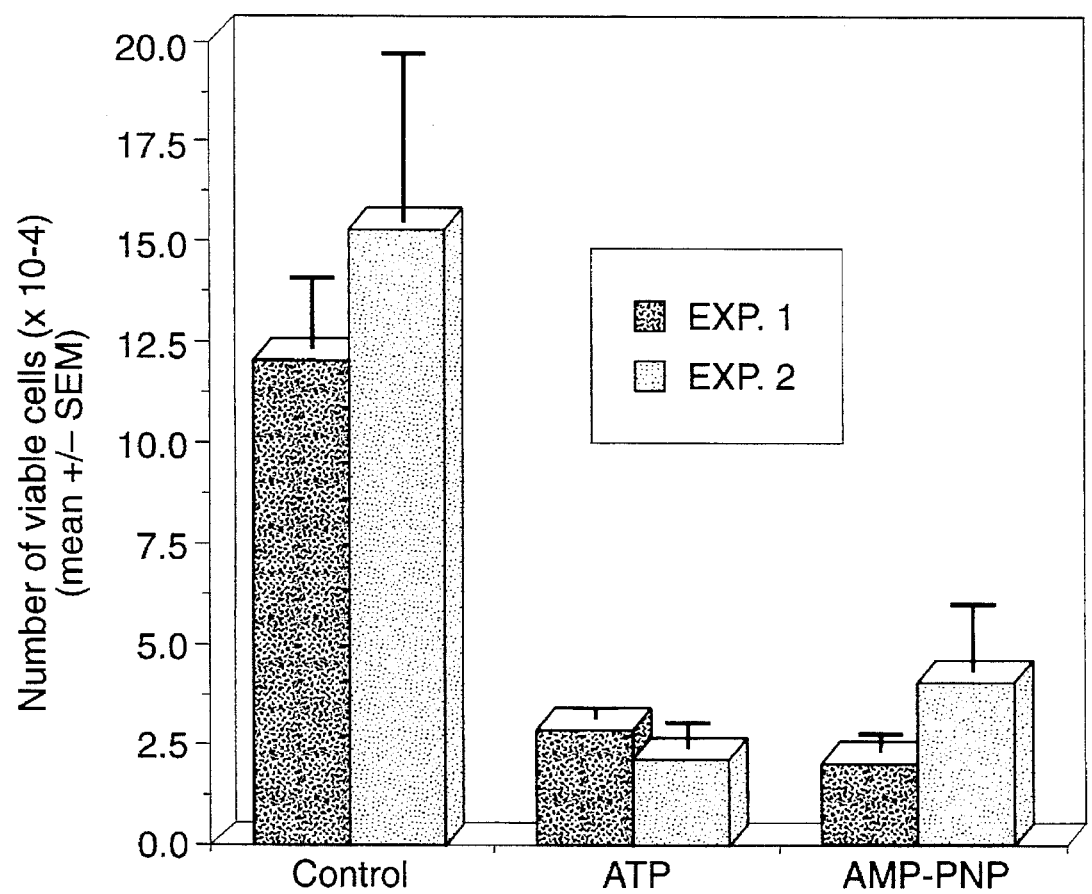
FIG. 12 shows the inhibition of growth of PC-3 cells in the presence of ATP and AMP-PNP. Cells treated for 5 days with 100 µM ATP or AMP-PNP versus untreated control cells.

Since purinergic receptor agonists induce massive mobilization of internal $Ca^{2+}$ stores and prolong this response through the opening of plasma membrane $Ca^{2+}$ channels, the effect of purinergic receptor stimulation on the growth of androgen-independent cells was examined. The cell lines DU145, PC-3, and PC-3M were incubated in the presence of ATP or the nonhydrolysable ATP analog adenylylimido-diphosphate (AMP-PNP), and cell growth was determined by hemacytometer counts of viable cells, with viability determined by trypan blue exclusion. The inhibition of growth after 5 days of treatment is shown in FIG. 11 (DU145) and FIG. 12 (PC-3). These data are the first showing that purinergic agonists inhibit the growth of prostate carcinoma cells.

To further document the purinergic agonist-induced growth inhibition, thymidine incorporation studies were performed in conjunction with hemacytometer cell counts, and the thymidine incorporation per cell of ATP and AMP-PNP treated PC-3 and PC-3M cells was determined. These studies, shown in Table 2, confirmed that purinergic agonists inhibit the growth of androgen-independent prostate carcinoma cells. Furthermore, these studies show that $^3$-thymidine incorporation is not inhibited when calculated on a per cell basis, despite the fact that cell growth was markedly inhibited. These data suggest that purinergic agonist inhibition of the growth of the prostate carcinoma cells is associated with, and may be mediated by, an increase in DNA strand breaks. It is of interest that normal prostate cells die in response to androgen withdrawal in a process called apoptosis, and this cell death resembles the cell death shown after treatment with purinergic agonists in two respects. Firstly, the death of normal prostate cells after androgen withdrawal is dependent on a rise in intracellular $Ca^{2+}$. Secondly, the death of normal prostate cells after androgen withdrawal is mediated by an increase in the number of DNA strand breaks. Thus, this technique should be therapeutically useful for circumventing the absence of androgen receptors on advanced prostate carcinoma cells. The results presented here represent the discovery of a surface receptor specifically expressed on advanced prostatic adenocarcinoma which, when activated, induces a mode of cell death that apparently utilizes that same intracellular pathway as the death that normal prostate cells undergo in response to the withdrawal of androgen.

TABLE 2

COMPARISON OF CELL NUMBER AND $^3$H-THYMIDINE INCORPORATION IN PC-3 AND PC-3M PROSTATE CARCINOMA

|  | cell # | | |
|---|---|---|---|
|  | (× 10−4) | cpm | cpm/cell |
| PC-3 | | | |
| Control | 23.0 | 5530 | 0.02 |
| ATP | 7.5 | 2729 | 0.04 |
| AMP-PNP | 0.5 | 307 | 0.06 |
| DbcAMP | 1.5 | 182 | 0.01 |
| PC-3M | | | |
| Control | 17.0 | 20665 | 0.12 |
| ATP | 3.0 | 3307 | 0.11 |
| AMP-PNP | 2.0 | 2790 | 0.14 |
| Ionomycin | 1.0 | 3920 | 0.39 |

Cells treated for 5 days (PC-3M) or 7 days (PC-3) with ATP (100 μM), AMP-PNP (100 μM), or ionomycin (1 μM) versus untreated control cells

NUDE MICE STUDIES

Figure 13:
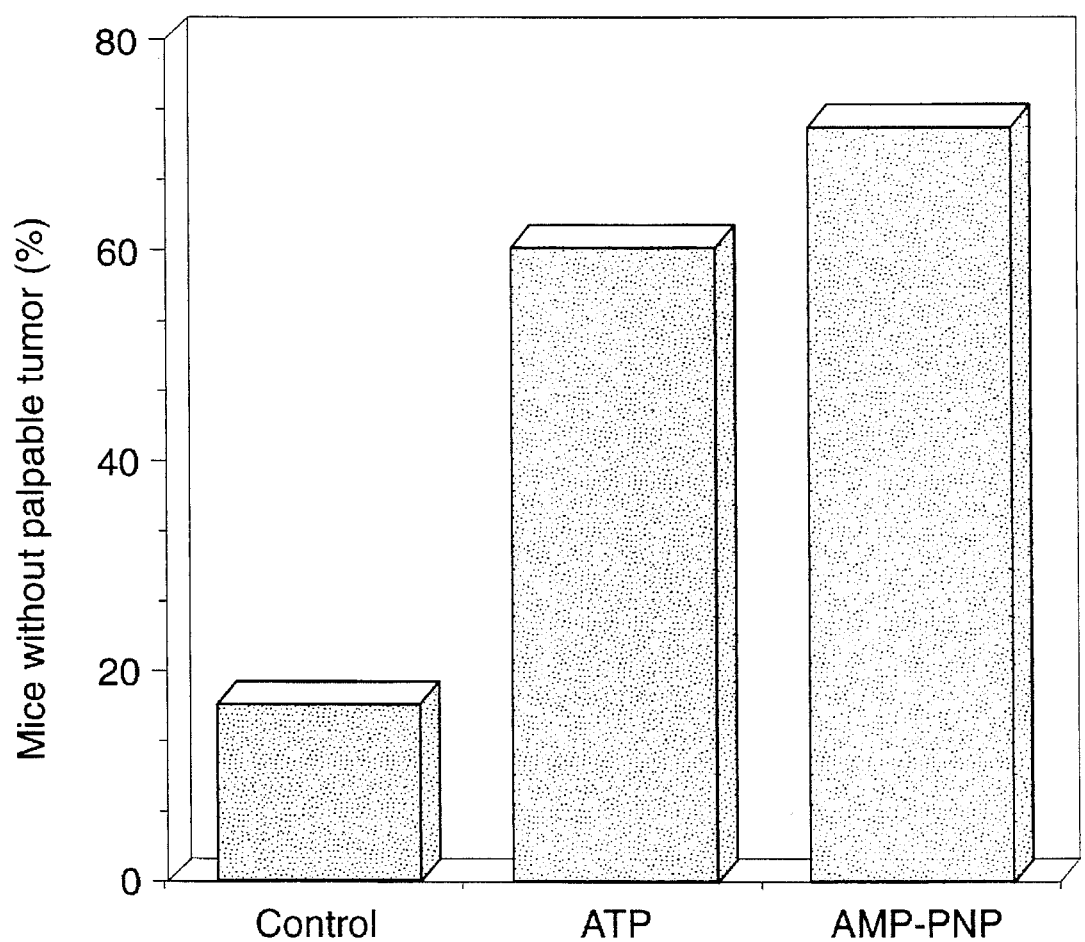
FIG. 13 shows the inhibition of PC-3 prostate carcinoma tumorigenesis by ATP and AMP-PNP. Athymic mice inoculated 1.22.90 with $1.5 \times 10^6$ cells pretreated in vitro×3 for 7 days, examined for palpable tumor on 2.16.90.

In further experiments, it has been found that purinergic agonist treatment inhibited the growth of androgen-independent prostate carcinoma cells in nude mice (FIG. 13). The cells were treated in vitro for 7 days, and then an equal number of untreated control cells, ATP treated, or AMP-PNP treated cells were inoculated subcutaneously into nude (athymic) mice.

Further nude mouse studies are presently being performed, using an implantable Alzet pump to provide the equivalent of a continuous infusion. The compounds will be administered orally, by continuous infusion, or by intermittent infusion, accompanied by pharmacologic studies to determine the optimal dose and schedule to obtain a steady state plasma concentration of approximately 100 μM.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A method for treating $P_2$ purinergic receptor-expressing ovarian, breast, or endometrial cancer in a subject, which comprises administering to the subject an effective ovarian, breast, or endometrial cancer cell growth inhibiting amount of a $P_2$ purinergic receptor agonist that is an analog of a purine nucleotide, said analog is a purine nucleotide which is substituted with an atom or chemical group at one or more hydroxyl or oxygen positions on a phosphate group in the said nucleotide, said atom or chemical group making said analog more resistant to hydrolysis than said purine nucleotide.

2. The method of claim 1, wherein said analog is an analog of an adenine nucleotide.

3. The method of claim 1, further comprising the administration of a $Ca^{2+}$ channel agonist.

4. The method of claim 3, wherein the $Ca^{2+}$ channel agonist is 1,4-dihydro-2,6-dimethyl-5-nitro-4-[2'-trifluoromethyl) phenyl]-3-pyrindine carboxylic acid methyl ester ((−) Bay K 8644).

5. The method of claim 1, wherein said cancer is breast cancer.

6. The method of claim 1, wherein said subject is human.

7. The method of claim 6, wherein said analog of an adenine nucleotide is administered to said human in an amount effective to achieve a steady-state plasma concentration of from about 0.5 µM to about 500 µM, and a peak plasma concentration from about 500 µM to 2 mM.

8. The method of claim 3, wherein the $Ca^{2+}$ channel agonist is administered to said human in an amount effective to achieve a steady-state plasma concentration of from about 0.5 µM to about 500 µM, and a peak plasma concentration from about 500 µM to 2 mM.

9. The method of claim 7, wherein said analog of an adenine nucleotide is an ATP analog.

10. The method of claim 9, wherein said ATP analog is selected from the group consisting of 5'adenylylimidodiphosphate, adenylyl ($\alpha,\beta$-methylene)-diphosphonate, adenylyl ($\beta,\gamma$-methylene)-diphosphonate and adenosine-5'-O-(3-thiophosphate).

11. The method of claim 7, wherein said analog of an adenine nucleotide is administered orally, by continuous infusion, or by intermittent infusion.

12. The method of claim 8, wherein the $Ca^{2+}$ channel agonist is administered orally, by continuous infusion, or by intermittent infusion.

13. The method of claim 1, wherein the atom or chemical group is a methylene, thiol, or imido group.

14. A method of inhibiting the growth of ovarian, breast, or endometrial cancer cells expressing $P_2$ purinergic receptors comprising:

exposing the ovarian, breast, or endometrial cancer cells expressing $P_2$ purinergic receptors to an effective growth-inhibiting amount of a $P_2$ purinergic receptor agonist that is an analog of a purine nucleotide, said analog is a purine nucleotide which is substituted with an atom or chemical group at one or more hydroxyl or oxygen positions on a phosphate group in said nucleotide, said atom or chemical group making said analog more resistant to hydrolysis than said purine nucleotide.

15. The method according to claim 14 wherein the cancer cells are breast cancer cells.

16. A method according to claim 14, wherein the atom or chemical group is a methylene, thiol, or imido group.

* * * * *